(12) United States Patent
Schmidt et al.

(10) Patent No.: US 6,468,563 B1
(45) Date of Patent: Oct. 22, 2002

(54) METHOD AND DEVICE FOR PRODUCING PHARMACEUTICAL FORMULATIONS CONTAINING AN EXTRACT

(75) Inventors: Peter C. Schmidt, Tubingen (DE); Karin Rocksloh, Kirchentellinsfurt (DE); Wolfgang Müller, Glienicke (DE); Markus Reher, Glienicke (DE); Salah Abu Abed, Berlin (DE)

(73) Assignee: Lichter Pharma AG, Berlin (DE)

( * ) Notice: Subject to any disclaimer, the term of this patent is extended or adjusted under 35 U.S.C. 154(b) by 0 days.

(21) Appl. No.: 09/581,684

(22) PCT Filed: Dec. 17, 1998

(86) PCT No.: PCT/DE98/03784

§ 371 (c)(1),
(2), (4) Date: Aug. 28, 2000

(87) PCT Pub. No.: WO99/32090

PCT Pub. Date: Jul. 1, 1999

(30) Foreign Application Priority Data

Dec. 18, 1997 (DE) .......................... 197 58 100

(51) Int. Cl.⁷ .......................... A61K 35/78; A61K 9/14; A61K 9/16; A61K 9/50

(52) U.S. Cl. ...................... 424/725; 424/400; 424/489; 424/490

(58) Field of Search ................................ 424/400, 489, 424/490, 725

(56) References Cited

U.S. PATENT DOCUMENTS 4,016,254 A * 4/1977 Seager ........................ 424/497
4,565,807 A * 1/1986 Uekama et al. ................ 514/58
5,496,561 A   3/1996 Okada et al. ................ 424/480
5,648,092 A * 7/1997 Weckenmann et al. ..... 424/464
5,739,165 A * 4/1998 Makino et al. ............. 514/570
5,851,550 A * 12/1998 Martin et al. ................ 424/464
5,914,128 A * 6/1999 Liebowitz et al. .......... 424/451

FOREIGN PATENT DOCUMENTS

| DE | 41 39 118 A1 | 6/1993 |
| EP | 0 348 509 A1 | 1/1990 |
| EP | 0 530 833 A1 | 3/1993 |

OTHER PUBLICATIONS

H. C. Ansel, et al., "Pharmaceutical Dosage Forms and Drug Delivery Systems", 5$^{th}$ Edition, pp. 169, 173–174, 1990.

Paul Heinz and Peter C. Schmidt, "Herstellung fester Arzneiformen aus Trockenextrakten", Jul. 1984, pp. 385–389, Stuttgart (with English summary).

E. Nurnberg, et al., "Arzneiformen", pp. 733–734; with translation of marked parts. 1993.

* cited by examiner

Primary Examiner—Christopher R. Tate
(74) Attorney, Agent, or Firm—Christie, Parker & Hale, LLP

(57) ABSTRACT

A process for producing rapidly disintegrating pharmaceutical formulations containing an extract is provided. The process comprises providing a dry powdered extract and a lubricant, compacting the powdered extract with the lubricant, using between about 0.5–10% lubricant by weight. The compacting is done using a device that yields flakes. The flakes are then crushed into granules, and the granules are compressed with conventional excipients such as bulking agents, glidants, disintegrants, flow regulators and other additives into pharmaceutical formulations.

19 Claims, No Drawings

METHOD AND DEVICE FOR PRODUCING PHARMACEUTICAL FORMULATIONS CONTAINING AN EXTRACT

BACKGROUND

The invention relates to a process for the production of extract-containing pharmaceutical formulations such as tablets, film-coated tablets, sugar-coated tablets inter alia.

Plant-based medicinal products contain in solid preparations dry extracts from herbal drugs which are generally produced by extraction with alcohol/water mixtures and subsequent evaporation and drying. The dosage of these extracts in each single dose may vary within wide limits. The extracts are hygroscopic and are difficult to compress into pharmaceutical formulations such as tablets or cores for coated tablets. The extracts normally contain mucilages which impede subsequent disintegration of the tablets, film-coated tablets or sugar-coated tablets.

In the state of the art, pharmaceutical formulations such as tablets or tablet cores for film-coated tablets and sugar-coated tablets are produced by direct tableting or previous granulation of the active ingredients and, where appropriate, excipients. Direct tableting is a simple process because the ingredients are merely mixed and compressed into tablets. This results in no exposure to moisture during the granulation, and hydrolysis processes are avoided. Likewise, temperature stress during drying of the granules is precluded.

However, direct tableting frequently fails with many extracts because of the poor flow characteristics and the poor compressibility of the extracts. To granulate the active ingredients, they are mixed with solvents or binder solutions and granulated in known devices and then dried.

Granulation by moistening with solvents or the use of binder solutions entails an increase in the particle size and standardization of the particle size distribution of the medicinal substances. At the same time, the flow characteristics of the granules are improved by comparison with the starting substances. It is likewise possible to achieve a greater accuracy of dosage in the tableting machine.

Aqueous granulation can be used only rarely for extract-containing products because extracts are prone, because of their high solubility and high hydrophilicity, to jamming or clogging very quickly during the granulation process.

Using organic solvents for granulation is at present difficult for toxicological and environmental reasons.

EP A 0 530 833 discloses a process for producing Kampo extract-containing hard gelantin capsules. This entails the Kampo extract being compressed in a first stage together with amounts between 0.5 and 1% by WEIGHT of magnesium stearate and other conventional excipients, and crushed and classified. The resulting granules are mixed with a further amount of magnesium stearate and packed into hard gelatin capsules. Addition of magnesium stearate to the granulated extract which has already been prepared that is to say, addition of magnesium stearate in the outer phase, is obligatory. This publication specifies that the addition of the magnesium stearate takes place not as a lubricant, but to improve the dissolving properties of the pharmaceutical hard gelatin capsules.

SUMMARY

The invention is based on the object of preparing extracts so that they can be satisfactorily incorporated in an amount of from 100 to 1000 mg of extract per single dose into pharmaceutical formulations such as tablets, film-coated tablets, sugar-coated tablets and the like, and are released from the pharmaceutical formulations within an appropriate time.

In the process according to the invention, the extract powders are compacted together with a lubricant. For this purpose, the extract powder is mixed with amounts of from 0.5 to 10% by weight of lubricants and is compacted. Amounts of 2–5% by weight of lubricants are preferably used in the compaction. Particularly suitable amounts of lubricant are 3% by weight.

The compaction takes place in devices suitable for this purpose. Thus, it is possible to compress the mixture to flakes between two rolls in a compactor. A pressure of from 20 to 120 kN is used for producing the compacts in the compactor. Preferred pressures are from 35 to 65 kN. Particularly suitable pressures are from 42 to 48 kN. With an effective width of the roll of 5 cm the resulting specific pressure is from 4 to 25 kN/cm.

To improve the compression, the device for the actual compaction can be preceded by a precompaction device. It is possible in this way, on use of a compactor, to employ one preceded by a precompaction screw. The precompaction screw is connected to the compactor and operates with the screw revolving at 20 to 60 revolutions/min. Preferred values for the number of revolutions are from 25 to 35 revolutions/min. The resulting flakes are then reduced in size while dried to granules of defined particle size. The reduction in size and granulation preferably take place in a screening machine.

The resulting granules are compressed to pharmaceutical formulations after addition of excipients such as dry binders, disintegrants and, where appropriate, flow regulators. The compaction of the extract with a lubricant means that no further lubricant is required in the outer phase. Addition of a flow regulator that increases capillary forces in the outer phase affords pharmaceutical formulations which have a shorter disintegration time and greater hardness compared with friability of the resulting pharmaceutical formulations.

DETAILED DESCRIPTION

The invention is to be explained in detail by means of examples.

The commercial products mentioned in the examples are specifically

| Name of the substance | Commercial product of the company | Composition |
| --- | --- | --- |
| Cellactose | Meggle Marke- | 75% lactose monohydrate 25% cellulose powder |
| Tablettier-hilfsmittel K | E. Merck KGaA | Cellulose powder |
| Ac-di-Sol | Lehmann & Voss & Co. | Crosslinked carboxymethyl-cellulose |
| Dynasan 1118 | Huls AG | Glycerol tristearate |
| Avicel PH 101 | Lehmann & Voss & Co. | Microcrystalline cellulose |
| Cab-O-Sil | Cabot GmbH | Colloidal silica |
| Kollidon CL | BASF AG | Crosslinked polyvinylpyrrolidone |

EXAMPLE 1

This example is intended to compare the values obtained for hardness and disintegration times for pharmaceutical formulations of compacted and non-compacted extract.

To produce the compact of extract powder and lubricant, 3% magnesium stearate is added as lubricant to the extract powder and mixed in a suitable mixer.

The compacts are produced from this mixture in a Pharmapaktor L 200/50 P. The compactor is equipped with concave smooth rolls, the effective width is 5 cm, and a pressure of 45 kN is used. This results in a specific pressure of 9 kN/cm width of roll. The rolls revolve at 10.3 revolutions/min. The compactor is also equipped with a cylindrical/conical precompaction screw for deaeration and precompaction of the powder composition. The screw revolves at 25 revolutions/min. On processing extracts without magnesium stearate, the extracts are introduced directly into the compactor.

The resulting flakes are then reduced in size to granules in a screening mill, for example an FC 200 screening mill with a screen of mesh width 1.5 mm.

The pharmaceutical formulation, in this case tablets, is produced in a Korsch Pharma 103 rotary tablet press with 3 punches at 20 revolutions/min and with varying pressure.

The formulas to be processed consist in the case of the non-compacted extract a) of:

| Ingredients | |
| --- | --- |
| Native extract (94%) | 531.9 mg |
| Cellactose | 99.9 mg |
| Tablettierhilfsmittel K | 27.1 mg |
| Ac-di-Sol | 28.0 mg |
| Dynasan 118 | 14.0 mg |
| Total weight | 700.0 mg | in the case of the compacted extract b) of

| Ingredients | |
| --- | --- |
| Compacted extract (with 3% magnesium stearate as lubricant) | 537.3 mg |
| Avicel PH 101 | 127.7 mg |
| Ac-di-Sol | 28.0 mg |
| Cab-O-Sil | 7.0 mg |
| Total weight | 700.0 mg |

The resulting products were compared for their hardness and disintegration time on use. The following values were obtained:

|  | Non-compact. extract | | | Comp. extract | | |
| --- | --- | --- | --- | --- | --- | --- |
| Pressure (kN) | 3.7 | 6.1 | 7.6 | 3.4 | 5.5 | 7 |
| Hardness N | 34.3 | 83.3 | 119.4 | 31.3 | 69.8 | 101.1 |
| Disintegration (min) | 37 | 44 | 47.5 | 17.5 | 31.5 | 33.5 |

The hardness of all the examples was determined in accordance with Ph. Eur. 1997 (European Pharmacopoeia 1997) using a Schleuniger 6 D hardness tester. The disintegration times were likewise determined in accordance with Ph. Eur. 1997.

The results show that the disintegration times obtained with non-compacted extract and lubricant in the outer phase were in all cases considerably longer than with compacted extract containing an addition of 3% magnesium stearate in the compact. The differences between the disintegration times for the non-compacted extract and the compacted extract are particularly distinct at low tableting pressures.

EXAMPLE 2

This example compares the values mentioned in Example 1 for the hardness and disintegration time of compacted extract with and without magnesium stearate in the compact.

The compacts used were produced as described in Example 1. Tableting likewise took place as described in Example 1.

The formulas consist of a) compact with 5% magnesium stearate b) compact without magnesium stearate (2% in the outer phase), c) compact without magnesium stearate (1% in the outer phase),

|  | a) | b) | c) |
| --- | --- | --- | --- |
| Compact. extract | 315.8 mg | 300.0 mg | 300.0 mg |
| Avicel PH 101 | 125.8 mg | 132.4 mg | 137.0 mg |
| Kollidon CL | 18.4 mg | 18.4 mg | 18.4 mg |
| Magnesium stearate | — | 9.2 mg | 4.6 mg |
| Total weight of each tablet | 460.0 mg | 460.0 mg | 460.0 mg |

The following results were obtained:

|  | a) | | b) | | c) | |
| --- | --- | --- | --- | --- | --- | --- |
| Pressure (kN) | 6 | 7.6 | 7.1 | 8.6 | 7.7 | 9.4 |
| Hardness (N) | 53.7 | 82.8 | 49.4 | 60.8 | 48.9 | 60.4 |
| Disintegration time (min) | 12.5 | 18.5 | 20.0 | 30.0 | 38.5 | 44 |

The resulting disintegration times show that considerably shorter disintegration times are obtained on incorporation of 5% magnesium stearate into the compact than with 1% or 2% magnesium stearate in the outer phase while magnesium stearate is absent from the compact. It is therefore unnecessary to use magnesium stearate in the outer phase as long as the compact contains a lubricant. Another advantage which emerges, when there is a large amount of magnesium stearate in the compact, is a shorter disintegration time of the tablets.

EXAMPLE 3

This example compares disintegration times of tablets which contain different lubricants and different amounts of lubricants in the compact.

The lubricants employed were, on the one hand, magnesium stearate and, on the other hand, Dynasan 118.

The production of the compacts and the tableting took place as in Example 1.

The formulas contain a) 5%, b) 3% and c) 1% lubricant in the compact.

|  | a) | b) | c) |
|---|---|---|---|
| Compact. extract | 335.9 mg | 329.0 mg | 322.3 mg |
| Avicel PH 101 | 105.7 mg | 112.6 mg | 120.1 mg |
| Ac-di-Sol | 18.4 mg | 18.4 mg | 18.4 mg |

The following results were obtained:

| | in the compact | | | | | |
|---|---|---|---|---|---|---|
| | 5% Mg stearate | 5% Dynasan | 3% Mg stearate | 3% Dynasan | 1% Mg stearate | 1% Dynasan |
| Pressure (kN) | 13.1 | 12.8 | 11.9 | 16.2 | 13.2 | 13.2 |
| Hardness | 81.8 | 80.4 | 85.4 | 96.8 | 89.5 | 89.7 |
| Disintegration (min) | 37.0 | 31.5 | 28.0 | 24.5 | 26.5 | 25.5 |

Comparison of the lubricants magnesium stearate and Dynasan 118 in the compact shows that, with identical hardnesses, the tablets with Dynasan 118 provide shorter disintegration times on average.

Additional lubrication in the outer phase is unnecessary.

The results obtained further show that with smaller amounts of lubricant in the formula for the compact the differences between the disintegration times obtained for the different lubricants approach one another.

Sufficiently short disintegration times with reliable lubrication in all the formulas are achieved with additions of 3% lubricant.

EXAMPLE 4

This example investigates the effect of additions of disintegrant on the disintegration time while the hardness varies.

The compacts and the tablets were produced as described in Example 1.

The formulas consist of:

| | | | |
|---|---|---|---|
| Compact. extract (with 5% Mg stearate) | 315.8 mg | 315.8 mg | 315.8 mg |
| Avicel Ph 101 | 144.2 mg | 125.8 mg | 125.8 mg |
| Ac-di-Sol | — | — | 18.4 mg |
| Kollidon CL | — | 18.4 mg | — |
| Total weight | 460.3 mg | 460.0 mg | 460.0 mg |

The following results were obtained:

| | without added disintegrant | | with 4% Kollidon CL | | with 4% Ac-di-Sol | |
|---|---|---|---|---|---|---|
| Pressure (kN) | 3.8 | 8.7 | 6 | 7.6 | 6.3 | 7.6 |
| Hardness (N) | 36.9 | 100.2 | 53.7 | 82.8 | 56.0 | 71.6 |
| Disintegration (min) | 19.0 | 85.0 | 12.5 | 18.5 | 19.0 | 26.5 |

The results show that the addition of 4% Kollidon CL as disintegrant in the outer phase causes a significant reduction in disintegration times compared with a tablet without added disintegrant. The effect of 4% Ac-di-Sol as disintegrant is not as pronounced as that of Kollidon CL at lower pressures but affords a distinct improvement compared with a tablet without added disintegrant at higher pressures and with harder tablets.

EXAMPLE 5

This examples investigates the effect of a flow regulator added to the outer phase on the hardness and the disintegration time.

The compacts and the tablets were produced as described in Example 1.

The formulas consist of:

| | | |
|---|---|---|
| Comp. extract with 1% Mg stearate added in the compact) | 322.3 mg | 322.3 mg |
| Avicel PH 101 | 114.7 mg | 119.3 mg |
| Kollidon CL | 18.4 mg | 18.4 mg |
| Cab-O-Sil M 5 | 4.6 mg | — |

The following results were obtained:

| | Compression mixture with flow regulator | | | Compression mixture without flow regulator | | |
|---|---|---|---|---|---|---|
| Pressure (kN) | 4.3 | 6.5 | 9.2 | 7.6 | 9.7 | 13.2 |
| Hardness (N) | 36.8 | 76.7 | 99.8 | 47.2 | 64.0 | 89.5 |
| Disintegration (min) | 9.5 | 15.5 | 25.0 | 13.5 | 21.0 | 26.5 |

The results show that a distinct increase in the hardness without a major change in the disintegration times is achieved through addition of Cab-O-Sil M5 as flow regulator. Over the entire range of pressures, harder tablets result on addition of 1% Cab-O-Sil as flow regulator.

What is claimed is:

1. A process for producing rapidly disintegrating pharmaceutical formulations, the process comprising:
   providing a dry powdered herbal extract and a lubricant,
   producing flakes by compacting the powdered extract with the lubricant in an amount ranging from 0.5 to 10% lubricant by weight using a device that yields flakes,
   crushing the flakes to granules, and
   compressing the resulting granules in the presence of a conventional excipient other than the lubricant to form a pharmaceutical formulation with an outer phase, wherein the excipient is a disintegrant added in an amount from 2 to 10% by weight to the outer phase upon compressing the mixture into the pharmaceutical formulation.

2. The process according to claim 1, wherein the device employed for the compression is a compactor, and a screening granulator is used for granulation of the flakes.

3. The process according to claim 1 or 2, wherein the device used for compression is a compactor having rolls, and a pressure of from 20 to 120 kN, with the rolls revolving at from 5 to 15 revolutions/min, is used for compression of the extract powder.

4. The process according to claim 1, wherein the device used for compression is a compactor, and the compactor has a precompaction screw for precompaction, which is operated with the screw revolving at from 20 to 60 revolutions/min.

5. The process according to claim 1, wherein the amount of herbal extract per single dose is from 100 to 1000 mg.

6. The process according to claim 1, wherein the amount of lubricant in the compact is between about 2 to 5% by weight.

7. The process according to claim 1, wherein the lubricant comprises magnesium stearate.

8. The process according to claim 1, wherein the lubricant comprises a glycerol fatty acid ester.

9. The process according to claim 1, wherein compressing the granules with the excipient forms an outer phase, and wherein the excipient is a flow regulator added at from 0.3 to 2.5% by weight to the outer phase upon compressing the mixture into the pharmaceutical formulation.

10. The process according to claim 1, wherein the granules are classified according to size after granulation.

11. The process according to claim 1, wherein the excipient is selected from bulking agents, glidants, disintegrants, and flow regulators.

12. The process according to claim 3 wherein the pressure is between about 35 and 65 kN.

13. The process according to claim 3 wherein the pressure is between about 42 and 48 kN.

14. The process according to claim 4 wherein the screw revolves between about 25 and 35 revolutions/min.

15. The process according to claim 6 wherein the amount of lubricant in the compact is about 3%.

16. The process according to claim 1 wherein a partial ester is the lubricant.

17. The process according to claim 1 wherein glycerol tristearate is the lubricant.

18. The process according to claim 1 wherein the disintegrant is added at 4% by weight.

19. The process according to claim 9 wherein the flow regulator is added at 1% by weight.

* * * * *